(12) United States Patent
Franks et al.

(10) Patent No.: US 7,632,872 B2
(45) Date of Patent: Dec. 15, 2009

(54) ANALGESIC AGENT FOR NEWBORN OR FETAL SUBJECTS

(75) Inventors: Nicholas Peter Franks, London (GB); Mervyn Maze, London (GB)

(73) Assignee: Protexeon Limited, Aldwych, London (GB)

( * ) Notice: Subject to any disclaimer, the term of this patent is extended or adjusted under 35 U.S.C. 154(b) by 108 days.

(21) Appl. No.: 10/524,316

(22) PCT Filed: Aug. 5, 2003

(86) PCT No.: PCT/GB03/03391

§ 371 (c)(1),
(2), (4) Date: Feb. 9, 2005

(87) PCT Pub. No.: WO2004/012749

PCT Pub. Date: Feb. 12, 2004

(65) Prior Publication Data

US 2006/0233885 A1    Oct. 19, 2006

(30) Foreign Application Priority Data

Aug. 5, 2002 (GB) .................. 0218153.5

(51) Int. Cl.
*A61K 33/00* (2006.01)
(52) U.S. Cl. .................. 514/816; 514/937; 514/959
(58) Field of Classification Search .................. 514/816, 514/937, 959
See application file for complete search history.

(56) References Cited

U.S. PATENT DOCUMENTS 5,099,834 A * 3/1992 Fishman ................ 128/203.12
6,197,323 B1 * 3/2001 Georgieff ................ 424/423
2002/0068764 A1 6/2002 Franks et al.

OTHER PUBLICATIONS

Fukura et al. (Prog. Neuro-Psychopharmacol. & Biol Psychiat. 2000, 24, 1357-1368).*
Lane et al. Science 1980, 210(4472), 899-901).*
Ohashi et al., "Xenon Exhibits Antinociceptive Effect on the Formalin Test in Newborn Fischer Rats", Anesthesiology Abstracts of Scientific Papers Annual Meeting, No. 2002, 2002, pages Abstract No. A-1291, XP001155998.
Ohashi et al., "Nitrous oxide exerts age-dependent antinociceptive effects in Fischer rats", vol. 100, No. 1-2, Nov. 2002, pp. 7-18, XP002261149.
Ohara et al., "A comparative study of the antinociceptive action of xenon and nitrous oxide in rats", Anesthesia and Analgesia, vol. 85, No. 4, 1997, pp. 931-936, XP009020357.

* cited by examiner

*Primary Examiner*—Ernst V Arnold
(74) *Attorney, Agent, or Firm*—Kenyon & Kenyon LLP (57) ABSTRACT

In a first aspect, the present invention relates to the use of xenon in the preparation of a medicament for providing analgesia in a newborn subject and/or a fetal subject. In a second aspect, the invention relates to a method of providing analgesia in a newborn subject, the method comprising administering to the subject a therapeutically effective amount of xenon. In a third aspect, the invention relates to a method of providing analgesia in a fetal subject, the method comprising administering to the mother of the fetal subject a therapeutically effective amount of xenon for both the mother and fetal subject.

18 Claims, 10 Drawing Sheets

ANALGESIC AGENT FOR NEWBORN OR FETAL SUBJECTS

CROSS-REFERENCE TO RELATED APPLICATIONS

The present application is a 371 application of PCT/GB03/03391, filed on Aug. 5, 2003, which claims priority to GB application Ser. No. 0218145.5, filed on Aug. 5, 2002.

The present invention relates to the field of analgesia. More specifically, the invention relates to an analgesic agent suitable for use in newborn and/or fetal subjects.

BACKGROUND

The human fetus and newborn are known to experience pain sensation [Anand K J S et al, New Engl J Med 1987; 317:1321-1329; Fitzgerald M, Br Med Bull 1991;47:667-75]. However, of greater concern is that untreated pain in the newborn may adversely affect development of the central nervous system resulting in long-term physiological and psychological consequences [Taddio A et al, Lancet 1997; 349: 599-603; Graham YP et al, Dev Psychopath 1999; 11:545-565; Anand K J S et al, Biol Neonate 2000; 77:69-82; Ruda M A et al, Science 2000; 289:628-630]. As a consequence, appropriate analgesic therapy is even more important in the anaesthetic management of the very young than in adults.

Nitrous oxide ($N_2O$) has been used for clinical anaesthesia in the young and the old for more than 150 years and remains the most commonly used anaesthetic gas. $N_2O$ usage in the paediatric surgical patient is based upon the assumption that its anaesthetic and analgesic efficacy matches that seen in adults [Eger E L, Nitrous Oxide/$N_2O$; Elsevier, New York, 1985]. However, the expectation that efficacious analgesic drugs in adults will exert the same beneficial effects in neonates has been challenged by our recent report that nitrous oxide ($N_2O$) is ineffective in neonatal rats because the immature pain pathways cannot activate the descending inhibitory pathway in response to nociceptive stimuli [Fitzgerald M et al, Brain Res 1986;389:261-70; van Praag H, Frenk H, Dev Brain Res 1991;64:71-76]. Experiments have shown that $N_2O$ lacks antinociceptive effects against thermal [Fujinaga M et al, Anesth Analg 2000; 91:6-10] and inflammatory [Ohashi Y et al, Pain 2002; 100:7-18] stimulation in rats under 3 weeks of age. If extrapolatable to humans, this would mean that $N_2O$ is ineffective as an analgesic agent in subjects up to and including the toddler stage. A similar rationale was thought to apply to the use of xenon as an analgesic agent.

The present invention seeks to provide an analgesic agent capable of providing effective pain relief in newborn and/or fetal subjects which alleviates one or more of the above-mentioned problems.

STATEMENT OF INVENTION

In a first aspect, the present invention relates to the use of xenon in the preparation of a medicament for providing analgesia in a newborn subject and/or a fetal subject.

In a second aspect, the invention relates to a method of providing analgesia in a newborn subject, the method comprising administering to the subject a therapeutically effective amount of xenon.

In a third aspect, the invention relates to a method of providing analgesia in a fetal subject, the method comprising administering to the mother of the fetal subject a therapeutically effective amount of xenon.

DETAILED DESCRIPTION

As mentioned above, in a broad aspect, the present invention relates to the use of xenon as an analgesic agent in newborn and/or fetal subjects.

More specifically, the invention relates to the use of xenon in the preparation of a medicament for providing analgesia in a newborn subject.

Surprisingly, it has been found that xenon is capable of providing effective analgesia in the newborn, despite prior art indications to the contrary. Indeed, it is to be noted that the prior art has neither disclosed nor suggested the use of xenon as an analgesic agent in neonatal subjects.

In a preferred embodiment, the newborn subject is a mammal in the first four weeks after birth. More preferably, the newborn subject is a mammal in the first two weeks, more preferably still, the first week after birth.

Even more preferably, the newborn subject is a human.

Xenon is a chemically inert gas whose anaesthetic properties have been known for over 50 years [Lawrence J H et al, J. Physiol. 1946; 105:197-204]. Since its first use in surgery [Cullen S C et al, Science 1951; 113:580-582], a number of research groups have shown it has an excellent pharmacological profile, including the absence of metabolic by-products, profound analgesia, rapid onset and recovery, and minimal effects on the cardiovascular system [Lachmann B et al, Lancet 1990; 335:1413-1415; Kennedy R R et al, Anaesth. Intens. Care 1992; 20:66-70; Luttropp H H et al, Acta Anaesthesiol. Scand. 1994; 38:121-125; Goto T et al, Anesthesiology 1997; 86:1273-1278; Marx T et al, Br. J. Anaesth. 1997; 78:326-327].

It has recently been discovered that xenon (which rapidly equilibrates with the brain) is an NMDA antagonist [Franks N P et al, Nature 1998; 396:324]. Mechanistic studies on cultured hippocampal neurons have shown that 80% xenon, which will maintain surgical anaesthesia, reduces NMDA-activated currents by up to 60%. This powerful inhibition of the NMDA receptor explains some of the important features of the pharmacological profile and is likely to be instrumental in the anaesthetic and analgesic effects of this inert gas.

The use of xenon in a pharmaceutical application is described in WO 00/76545, while the use of xenon as a neuroprotectant is described in WO 01/08692, the contents of which are incorporated herein by reference. Neither patent application discloses the possibility of xenon being an effective analgesic for newborn or fetal subjects.

The advantage of using an inert, volatile gas such as xenon as an analgesic agent is that the molecule can be rapidly eliminated via respiration. Xenon is currently thought to be a potential replacement for $N_2O$ [Rossaint R et al, Anesthesiology 2003;98:6-13]. In humans, xenon has a minimum alveolar concentration (MAC) of 71% atm [Lynch C et al, Anesthesiology 2000;92:865-70] which is even lower in elderly female patients (51% atn) [Goto T et al, Anesthesiology 2002;97:1129-32] and thus is more potent than $N_2O$ (MAC=104%) [Hornbein T F et al, Anesth. Analg. 1982;61: 553-6]. Xenon has faster induction and emergence [Goto T et al, Anesthesiology 1997;86:1273-8; Rossaint R et al, Anesthesiology 2003;98:6-13] due to its very low blood gas partition coefficient (0.115) [Goto T et al, Br J Anaesth 1998;80: 255-6], is devoid of teratogenic effects [Lane G A et al, Science 1980;210:899-901; Burov N E et al, Anesteziol Reanimatol 1999;6:56-60], is less harmful to the environment [Goto T, Can J Anaesth 2002:49: 335-8], and exhibits a lower risk of diffusion hypoxia [Calzia E et al, Anesthesiology 1999;90:829-3].

Studies by the applicant investigated the efficacy of xenon against formalin-induced nociception as reflected by behaviour and c-Fos expression (a marker of neuronal activation) in cohorts of rats at various ages. Further details of these experiments are outlined in the accompanying Examples.

In brief four cohorts of Fischer rats aged, 7, 19, 28 and greater than 77 days (adult), were exposed to either air or 70% xenon. Formalin plantar testing was used to mimic surgical stimulation, and this was assessed using immunohistochemical (c-Fos staining) and behavioral methods. Formalin administration produced a typical nociceptive response observed both behaviorally and immunohistochemically in each age group during exposure to air. However, these responses were significantly attenuated by xenon; in other words, xenon was shown to exert an antinociceptive response against formalin injection in Fischer rats at each of four developmental stages, i.e. at days 7, 19 and 28 day as well as in adults. These data are qualitatively different from those recently reported with $N_2O$ [Ohashi Y et al, Pain 2002;100: 7-18] in which no antinociceptive effect (neither behaviorally nor immunohstochemically) was noted in animals younger than 23 days old.

The present invention further relates to the use of xenon in the preparation of a medicament for providing analgesia in a fetal subject. In this embodiment of the invention, the xenon is preferably administered to the mother prior to or during labour.

During birthing, the fetus is subjected to mechanical stress which results in the activation of pain pathways. The present invention demonstrates that the impact of the activation of pain processing pathways in fetal subjects can be mitigated by the administration of xenon.

It is notable that to date, there has been no teaching or suggestion in the prior art to indicate that xenon could be used to provide analgesia in fetal subjects.

In one preferred embodiment, the xenon is used in combination with one or more other pharmaceutically active agents. The agent may be any suitable pharmaceutically active agent including anaesthetic or sedative agents which promote GABAergic activity. Examples of such GABAergic agents include isoflurane, propofol and benzodiazapines.

The xenon may also be used in combination with one or more other analgesic agents. Suitable analgesic agents may include alpha-2 adrenergic agonists, opiates or non-steroidal antiinflammatory drugs. Examples of suitable alpha-2 adrenergic agonists include clonidine, detomidine, medetomidine, brimonidine, tizanidine, mivazerol, guanabenz, guanfacine or dexmedetomidine.

The medicament of the present invention may also comprise other active ingredients such as L-type calcium channel blockers, N-type calcium channel blockers, substance P antagonists, sodium channel blockers, purinergic receptor blockers, or combinations thereof.

In one highly preferred embodiment of the invention, the xenon is administered by inhalation. More preferably, the xenon is administered by inhalation of a 20-70% v/v xenon/air mixture.

In another preferred embodiment, the medicament is in liquid form. For parenteral administration, the medicament may be used in the form of a sterile aqueous solution which may contain other substances, for example enough salts or monosaccharides to make the solution isotonic with blood.

In a more preferred embodiment, the xenon is used in combination with a pharmaceutically acceptable carrier, diluent or excipient.

Acceptable carriers or diluents for therapeutic use are well known in the pharmaceutical art, and are described, for example, in Remington's Pharmaceutical Sciences, Mack Publishing Co. [A. R. Gennaro edit. 1985].

The choice of pharmaceutical carrier, excipient or diluent can be selected with regard to the intended route of administration and standard pharmaceutical practice. Examples of suitable carriers include lactose, starch, glucose, methyl cellulose, magnesium stearate, mannitol, sorbitol and the like. Examples of suitable diluents include ethanol, glycerol and water.

The medicament may comprise as, or in addition to, the carrier, excipient or diluent any suitable binder(s), lubricant(s), suspending agent(s), coating agent(s), solubilising agent(s). Examples of such suitable excipients for the various different forms of pharmaceutical compositions described herein may be found in the "Handbook of Pharmaceutical Excipients, $2^{nd}$ Edition, (1994), Edited by A Wade and P J Weller.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Up to now, a significant problem which has impeded the use of xenon as a new anaesthetic is its high cost and the need to use complex apparatus to minimise the volume used (low-flow systems), along with the need to scavenge the gas for reuse. A further problem is that the potency of xenon is relatively low. As a consequence, it had been suggested that volatile general anaesthetics may be solubilised in a lipid emulsion and administered intravenously [Eger R P et al, Can. J. Anaesth. 1995; 42:173-176]. It is known in the art that local anaesthesia can be induced by intradermally injecting microdroplets of a general anaesthetic in a liquid form [Haynes D H, U.S. Pat. Nos. 4,725,442 and 44,622,219]. Typically these microdroplets are coated with a unimolecular phospholipid layer and remain stable in physiologically-compatible solutions. A similar approach is described in a recent patent application which proposes that xenon might be administered in this fashion [Georgieff M, European Patent Application No. 864329-A1].

Thus, in an even more preferred embodiment, the medicament is in the form of a lipid emulsion. By way of example, an intravenous formulation typically contains a lipid emulsion (such as the commercially available Intralipid®10, Intralipid®20, Intrafat®, Lipofundin®S or Liposyn® emulsions, or one specially formulated to maximise solubility) to sufficiently increase the solubility of the gas or volatile anaesthetic to achieve the desired clinical effect. Further information on lipid emulsions of this sort may be found in G. Kleinberger and H. Pamperl, Infusionstherapie, 108-117 (1983) 3.

The lipid phase of the present invention which dissolves or disperses the gas is typically formed from saturated and unsaturated long and medium chain fatty acid esters containing 8 to 30 carbon atoms. These lipids form liposomes in aqueous solution. Examples include fish oil, and plant oils such as soya bean oil thistle oil or cottonseed oil. The lipid emulsions of the invention are typically oil-in-water emulsions wherein the proportion of fat in the emulsion is conventionally 5 to 30% by weight, and preferably 10 to 20% by weight. Oil-in-water emulsions of this sort are often prepared in the presence of an emulsifying agent such as a soya phosphatide.

The lipids which form the liposomes of the present invention may be natural or synthetic and include cholesterol, glycolipids, sphingomyelin, glucolipids, glycosphingolipids, phosphatidylcholine, phosphatidylethanolamine, phosphatidylserine, phosphatidyglycerol, phosphatidylinositol.

The lipid emulsions of the present invention may also comprise additional components. These may include antioxidants, additives which make the osmolarity of the aqueous phase surrounding the lipid phase isotonic with the blood, or polymers which modify the surface of the liposomes.

It has been established that appreciable amounts of xenon maybe added to a lipid emulsion. Even by the simplest means, at 20° C. and normal pressure, xenon can be dissolved or dispersed in concentrations of 0.2 to 10 ml or more per ml of emulsion. The concentration of dissolved gas is dependent on a number of factors, including temperature, pressure and the concentration of lipid.

The lipid emulsions of the present invention may be loaded with a gaseous or volatile anaesthetic. In general, a device is filled with the emulsion and anaesthetics as gases or vapours passed through sintered glass bubblers immersed in the emulsion. The emulsion is allowed to equilibrate with the anaesthetic gas or vapour at a chosen partial pressure. When stored in gas tight containers, these lipid emulsions show sufficient stability for the anaesthetic not to be released as a gas over conventional storage periods.

The lipid emulsions of the present invention may be loaded so that the xenon is at the saturation level. Alternatively, the xenon may be present in lower concentrations, provided, for example, that the administration of the emulsion produces the desired pharmaceutical activity.

In one preferred embodiment, the medicament is in a form suitable for delivery intravenously (either by bolus administration or infusion), neuraxially (either subdural or subarachnoid) or transdermally.

The medicament of the present invention may also be administered in the form of an ointment or cream (lipid emulsion or liposomes) applied transdermally. For example, the medicament of the present invention may be incorporated into a cream consisting of an aqueous emulsion of polyethylene glycols or liquid paraffin. Alternatively, the medicament of the present invention may be incorporated, at a concentration of between 1 and 10% by weight, into an ointment consisting of a white wax or white soft paraffin base together with such stabilisers and preservatives as may be required. These ointments or creams are suitable for the local alleviation of pain and may be applied directly to damaged tissue, often with the aid of an optionally air-tight wound closure.

The concentrations employed in the medicament formulation may be the minimum concentration required to achieve the desired clinical effect. It is usual for a physician to determine the actual dosage that will be most suitable for an individual patient, and this dose will vary with the age, weight and response of the particular patient. There can, of course, be individual instances where higher or lower dosage ranges are merited, and such are within the scope of this invention.

The medicament of the present invention may be for human administration or animal administration.

Thus, the medicament of the present invention may also be used as an animal medicament. In this regard, the invention further relates to the use of xenon in the preparation of a veterinary medicament for providing analgesia in newborn animals. Preferably, the medicament of the present invention further comprises a veterinarily acceptable diluent, excipient or carrier.

For veterinary use, the medicament of the present invention, or a veterinarily acceptable formulation thereof, is typically administered in accordance with normal veterinary practice and the veterinary surgeon will determine the dosing regimen and route of administration which will be most appropriate for a particular animal.

A further aspect of the invention relates to a method of providing analgesia in a newborn subject, the method comprising administering to the subject a therapeutically effective amount of xenon.

Yet another aspect of the invention relates to a method of providing analgesia in a fetal subject, the method comprising administering to the mother of the fetal subject a therapeutically effective amount of xenon. Preferably, the xenon is administered in an amount which is therapeutically effective for both the mother and the fetal subject.

In a preferred embodiment, the xenon is administered to the mother prior to or during labour. Preferably, the xenon alleviates the pain associated with the mechanical stress experienced by the fetus during labour.

Advantageously, administering xenon to the fetus via the mother has the concomitant benefit of alleviating labour pain experienced by the mother during delivery. Thus, the administration of xenon to the mother prior to or during labour has the dual effect of providing pain relief to both the fetus and the mother.

The present invention is further described by way of the following non-limiting examples and with reference to the following Figures, wherein:

FIG. 1A shows a section treated with air/formalin, whereas FIG. 1B shows a section treated with xenon/formalin.

FIG. 2A shows a section treated with air/formalin, whereas FIG. 2B shows a section treated with $N_2O$/formalin.

FIG. 6 shows the number (mean±SEM, n=4) of c-Fos positive cells at the lumbar level in response to formalin injection from the four age-groups animals receiving either air (black bar) or 70% xenon /20% $O_2$/10% $N_2$ (Xe) (dot bar) or in response to saline injection from the four age-groups receiving air (white bar). *$P<0.01$, **$P<0.001$ relative to Air+formaline group at the corresponding region. +$P<0.01$, ++$P<0.001$ relative to Xenon+formalin. The figures in the left column represent c-Fos expression ipsilaterally associated with injection and those in the right column represent c-Fos expression contralaterally associated with injection. From 19-day-old to adult, laminae I-II (superficial area), laminae II-IV (nucleus proprius area), laminae V-VI (neck area) and laminae VII-X (ventral area) in the spinal cord section is presented by A/B, C, D and E as equivalent to the five regions in 7-day-old pups.

EXAMPLES

Example 1

The analgesic efficacy of xenon was investigated in a neonatal rat pup. A 7 day neonatal rat pup is known to be developmentally equivalent to a human full term fetus with respect to pain processing pathways.

A 7 day old rat was injected with formalin into the hindpaw during exposure to either air or xenon (70% v/v). 90 minutes later the animal was killed and the spinal cord removed; evidence of activation of pain-processing pathways by formalin was sought by counting the number of cFos positive neurones in the dorsal horn of the spinal cord.

Figure 1:
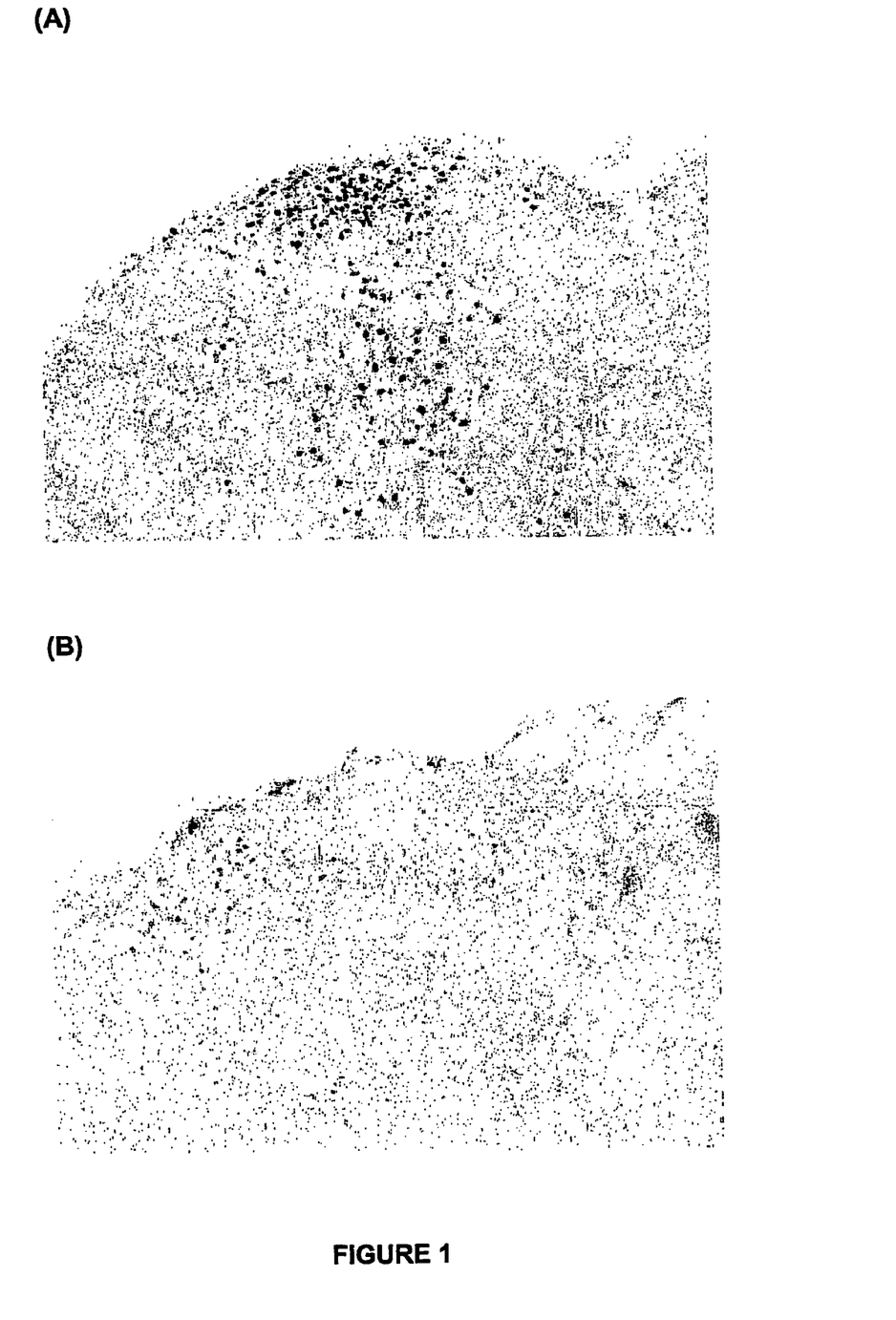
FIG. 1 shows cross sections of the spinal cord at the lumbar level stained for c-Fos in 7 day-old Fischer rats after receiving formalin.
Figure 2:
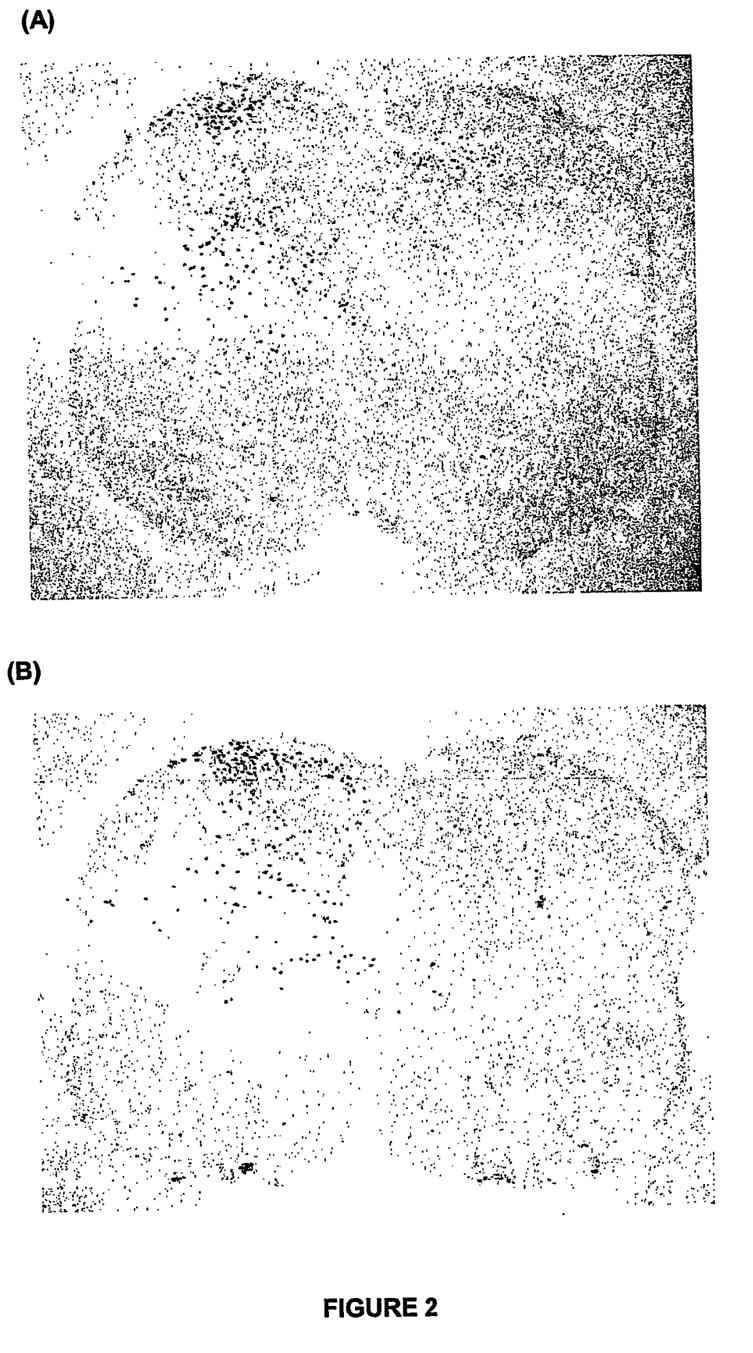
FIG. 2 shows cross sections of the spinal cord at the lumbar level stained for c-Fos in 7 day-old Fischer rats after receiving formalin.

In FIG. 1, xenon almost completely attenuated formalin-induced c-Fos positive neurones (air). By comparison a normally analgesic dose of nitrous oxide in the adult rat did not change formalin-induced c-Fos positive neurones (FIG. 2).

From the results, it can be concluded that xenon interrupts pain processing so that pain signals will not travel to the brain and hence pain, as well as the long-term consequences of untreated pain, is mitigated in the neonatal population.

Example 2

Materials and Methods

General Procedures and Animals

The study protocol was approved by the Home Office (UK), and all efforts were made to minimize animal suffering and the number of animals used. Fischer rats were used for the entire study (B&K Universal, Grimston Aldbrough Hull, UK). The rats were provided ad libitum food and water, and artificial lighting between 6 a.m. and 6 p.m. The age of each animal was determined from the body weight, based on a previously established growth curve (Hashimoto et al., 2002). (The date of birth was defined as 0 day-old.) Experiments were performed on rat pups of 7, 19, 28 day-old and on adult rats (11-12 week-old).

Within each age-group, there were three cohorts (n=3 - 4) "Air+formalin", "Xenon+formalin" and "Air+saline" cohorts. In the Air+formalin group, animals exposed to air were injected with 5% formalin into the plantar surface of their left hind paw subcutaneously. In the Xenon+formalin group, animals exposed to 70% Xe/20% $O_2$/10% $N_2$ were injected with 5% formalin as described above. In the Air+saline group, animals exposed to air were injected with saline as above. The volumes of formalin or saline injected were adjusted for each age group as previously reported [Ohashi Y et al, Pain 2002;100:7-18] and were as follows: 10 µl for 7 days old; 15 µl for 19 days old; 20 µl for 28 days old; 50 µl for adults.

Gas Exposure

Figure 3:
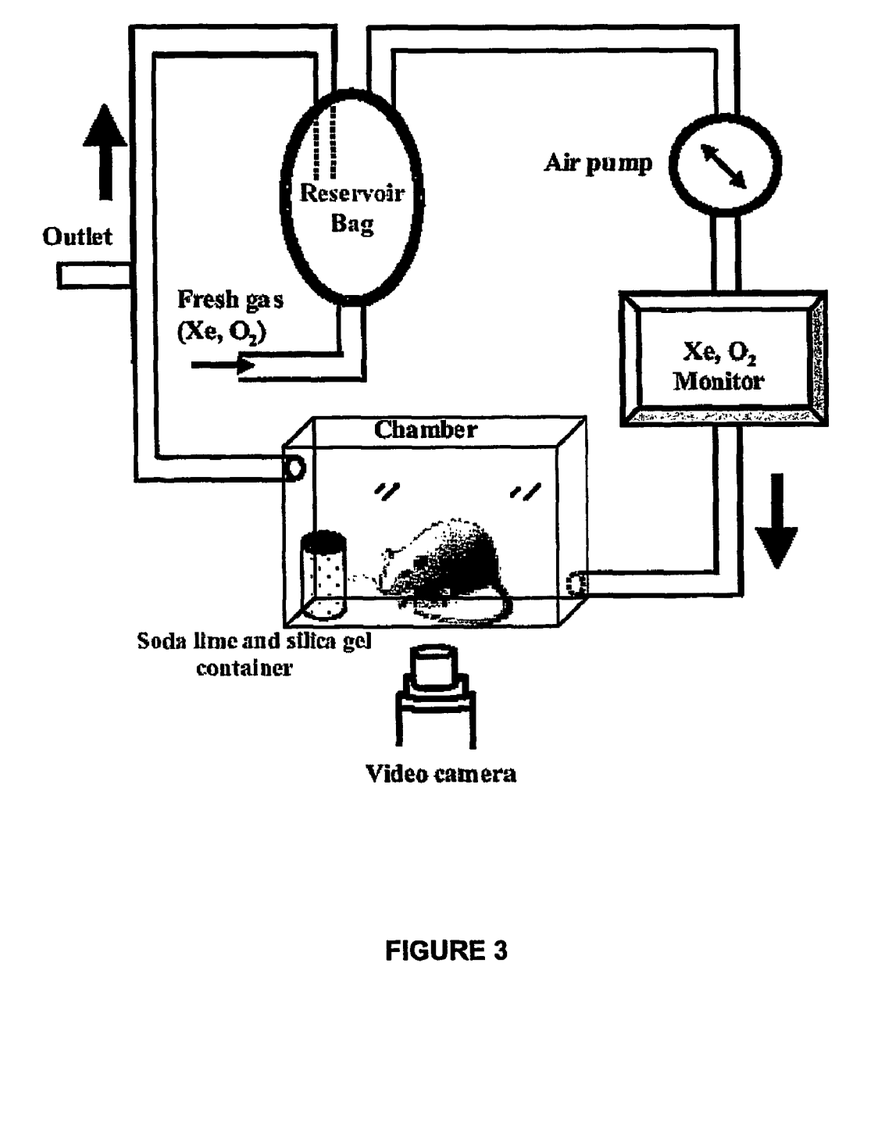
FIG. 3 shows a schematic diagram of the experimental apparatus and gas delivery closed circle system. This system consisted of an anaesthetic chamber, a rubber bag, an air pump and a xenon monitor (Model 439xe, Air product, UK).

A recirculating system for exposure to the gas was constructed to minimise xenon consumption (FIG. 3). The circuit was flushed with gas (either air or xenon/oxygen/nitrogen) at a flow rate of 4 l/min and after the desired gas concentrations were achieved, the flow rate was reduced to 40 ml/min for the remainder of the experimental period. The carbon dioxide level and the humidity were kept less than 0.6% and 50% respectively with soda lime and silica gel. Formalin or saline was administered 15 min after gas exposure; thereafter, animals were exposed to the gas mixture for a further 90 min.

Nociceptive Intensity Scoring

Immediately after injection of formalin, behavior was recorded for 60 min with a video camera (MegaPixel, Digital Handycam, Sony) positioned approximately 50 cm beneath the floor of the chamber to allow an unobstructed view of the paws (visible via a television monitor) and to facilitate recording of animal behavior. The chamber and holding area for pups waiting to be tested were maintained at room temperature throughout the experiment.

Nociceptive behavior was assessed in the 7-d old pups for the presence ("1") or absence ("0") of flexion, shaking, and whole body jerking per epoch of time [Teng C J et al, Pain 1998;76:337-47] and calculated as [Nociceptive score=T/300, where T is the duration (sec.) of nociceptive behavior exhibited during consecutive 300 sec post-injection epochs.]

Older rat pups were scored across four categories of pain behavior after xenon administration: no pain (the injected paw was in continuous contact with floor="0"), favoring (the injected paw rested lightly on the floor="1"), lifting (the injected paw was elevated all the time="2") and licking (licking, biting or shaking of the injected paw="3") [Teng C J et al, Pain 1998;76:337-47] and calculated as [Nociceptive score= (T1+[T2×2]+[T3×3])/300, where T1, T2 and T3 are the durations (sec) spent in categories 1, 2 or 3 per 300 sec epoch].

Immunohistochemical Staining and Quantitative Counting of c-Fos

Ninety min after the formalin injection, animals were deeply anesthetised with pentobarbital (100 mg/kg, i.p.) and perfused with 4% paraformaldehyde. The whole spinal cord was removed. The lumbar enlargement was sectioned transversely at 30 µm and then was stained for c-Fos as previously described [Ma D et al, Br J Anaesth 2002;89:73946]. Briefly, sections were incubated for 30 min in 0.3% $H_2O_2$ in methanol and thereafter washed three times in 0.1M phosphate buffered saline (PBS). Following this, the sections were incubated for 1 hour in a "blocking solution" consisting of 3% donkey serum and 0.3% Triton X in PBS (PBT) and subsequently incubated overnight at 4° C. in 1:5,000 goat anti-c-Fos antibody (sc-52-G, Santa Cruz Biotechnology, Santa Cruz, Calif.) in PBT with 1% donkey serum. The sections were then rinsed 3 times with PBT and incubated with 1:200 donkey anti-goat IgG (Vector laboratories, Burlingame, Calif.) in PBT with 1% Donkey serum for 1 hour. The sections were washed again with PBT and incubated with avidin-biotin-peroxidase complex (Vector Laboratories) in PBT for 1 hour. The sections were rinsed 3 times with PBS and stained with 3,3'-diaminobenzidine (DAB) with nickel ammonium sulphate in which hydrogen peroxide was added (DAB kit, Vector Laboratories). After the staining was completed, the sections were rinsed in PBS followed by distilled water and mounted, dehydrated with 100% ethanol, cleaned with 100% xylene and covered with cover slips.

Photomicrographs of three sections per each animal were scored for c-Fos positive neurons by an observer who was blinded to the experimental treatment. For the purpose of localizing the c-Fos positive cells to functional regions of the spinal cord, each section was divided into A/B (laminae I-II or the superficial area), C (laminae II-IV or nucleus proprius area), D (laminae V-VI or the neck area and E (laminae VII-X or the ventral area) [Yi D K et al, Pain 1995;60:257-265].

Data Analysis

The nociceptive intensity scoring against time in each animal was plotted and the area under curve (over a 60 min time period) (AUC) from each animal was calculated. The mean of c-Fos positive neurons for three representative sections in each region as described above was the aggregate score for each animal. The results of nociceptive intensity or c-Fos positive neurons are reported as means±SEMs. The statistical analysis was performed by one-way analysis of variance, followed by Newman-Keuls test. A p value <0.05 was regarded as statistically significant.

Results

Behavioral Nociceptive Response

Figure 4:
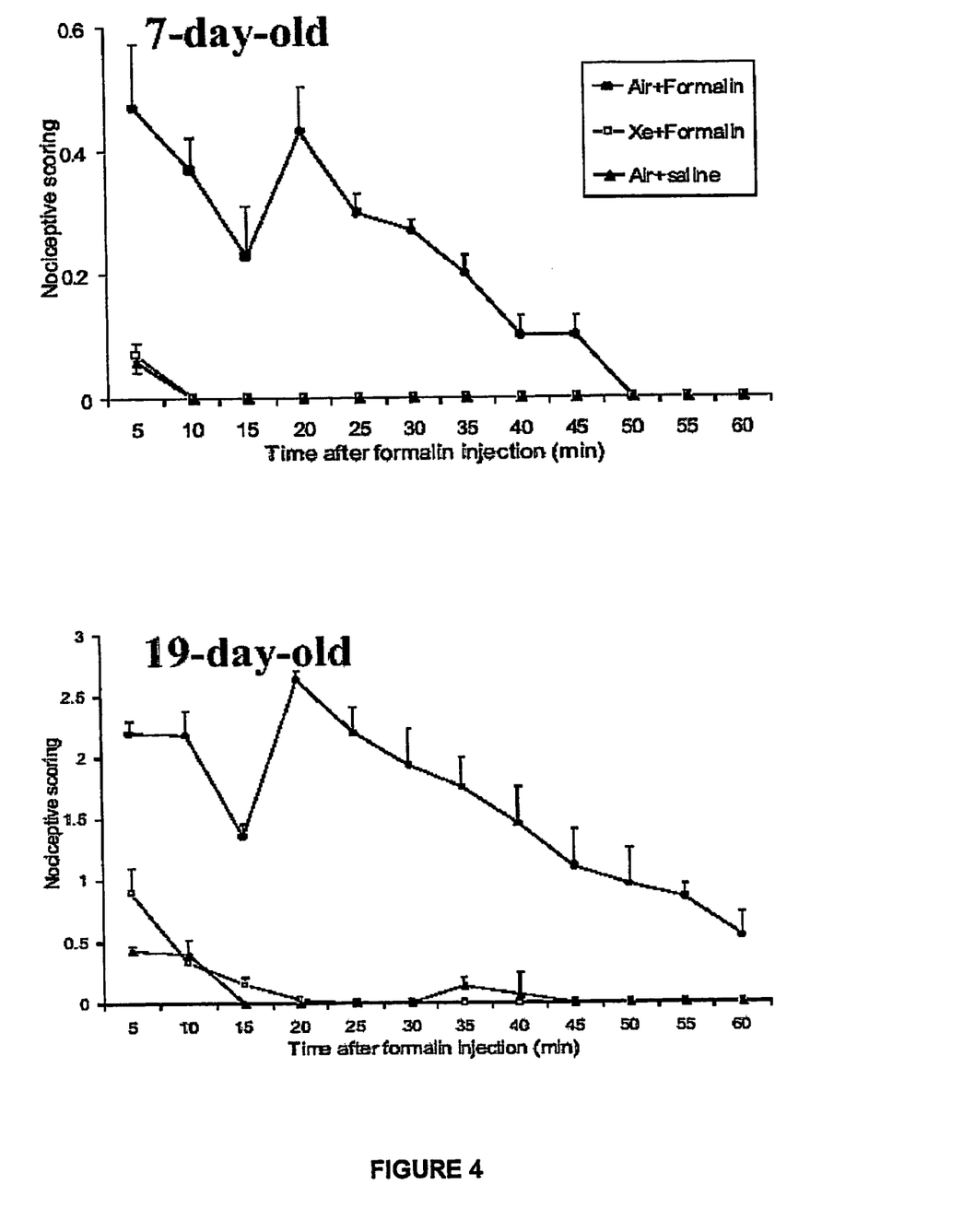
FIG. 4 shows nociceptive scoring curves from the four aged-groups in 7, 19, 28 olds Fischer pups and adults with two sub-treatments (Air+Formalin and Xe+Formalin). The ordinate reflects nociceptive intensity (lower values indicates less nociceptive behavior). The abcissa indicates the time period after formalin injection (min). The classical biphasic behavioural response to formalin can be seen in the group receiving air.

The time course of the nociceptive response of each cohort in each age category is presented in FIG. 4. Following injection with saline, the animals exposed to air exhibited a non-specific nociceptive behavior (score 1) involving the injected paw for a period of approximately two minutes duration. A biphasic nociceptive response is induced by formalin injection in each of the age groups administered air. The AUC data are presented in Table 1.

During the pre-injection period, 7 day-old rats exposed to air were awake and active. Following injection with formalin, the animals exhibited intense nociceptive behaviour (violent kicking, flexion and shaking of the injected paw) for up to 50 minutes but the exhibition of painful behavior appeared to be less than that seen with adult animals. Those rats exposed to xenon exhibited only mild nociceptive behaviour for the first two minutes after formalin injection followed by no further movement for the rest of the 60-min observation period. The AUC for the group exposed to xenon was significantly different from the group exposed to air (P<0.001; Table 1).

Following injection with formalin, the 19 day-old animals exposed to air exhibited intense nociceptive behaviour, which was biphasic, persisting for the majority of the observation period before gradually decreased (FIG. 4: 19 day old). There was a significant decrease in nociceptive behaviour exhibited by the animals that were exposed to xenon (P<0.01) (Table 1). In the 28 day-old cohort, animals exposed to air exhibited biphasic nociceptive behaviour; in the presence of xenon the nociceptive behaviour was significantly less intense (P<0.001) (Table 1). The nociceptive behaviour exhibited by adult rats in response to formalin was less intense with xenon than air exposure (P<0.001) (Table 1).

Immunohistochemical Nociceptive Response

Nociceptive Stimuli Induced c-Fos Expression

Figure 5:
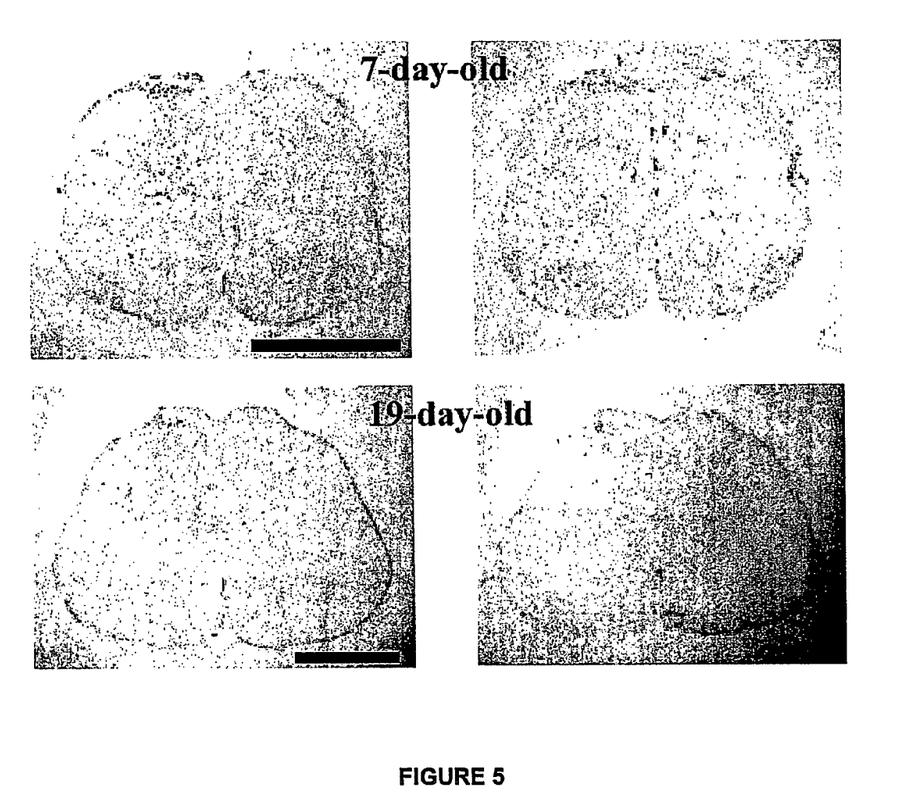
FIG. 5 shows a representative section from the spinal cords at the lumbar level of the spinal cord showing c-Fos response to formalin injection in neonatal rat pups aged 7, 19, 28 days and in an adult receiving either air (left column) or xenon (right column).
Figure 6:
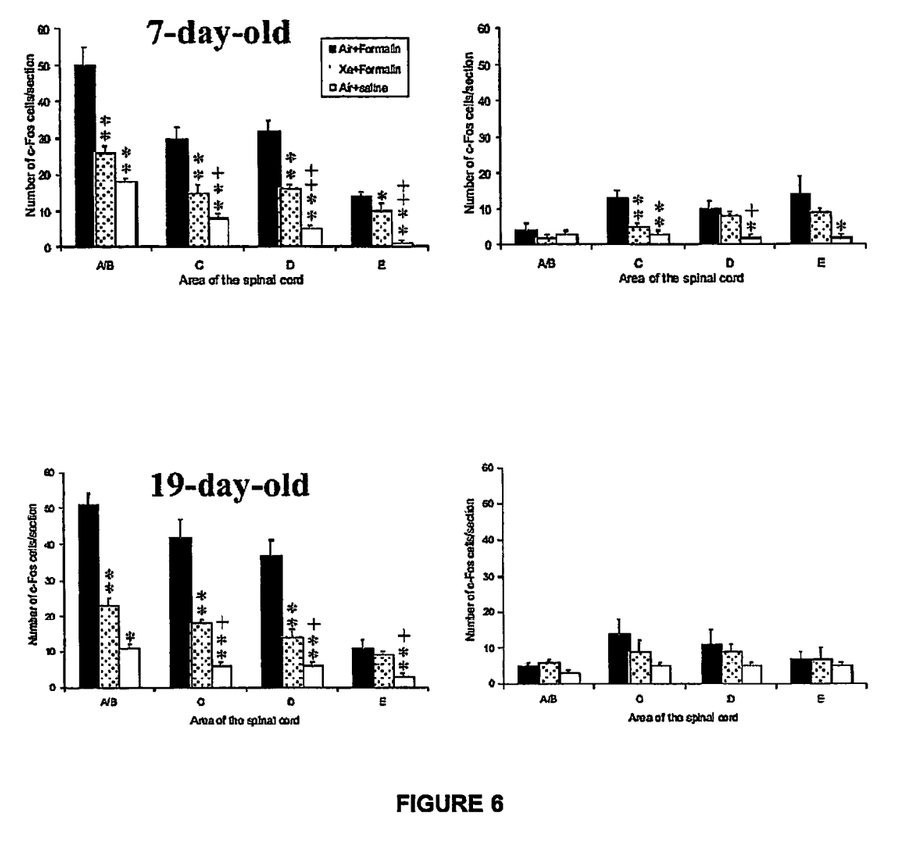

Formalin-induced c-Fos expression at the lumbar level of the spinal cord ipsilateral to the site of injection increased in all age groups. Exposure to xenon significantly suppressed c-Fos expression. In the 7 day-old pups, xenon exposure reduced c-Fos expression in response to formalin by 48% in laminae A/B (P<0.001), by 50% in lamina C (P<0.001), by 50% in lamina D (P<0.001) and by 28% in lamina E (P<0.01). In the 19 day-old rats xenon suppressed mean c-Fos expression in response to xenon by 55% in laminae I-II (P<0.001), by 57% in lamina III-IV (P<0.001) and by 62% in lamina V-VI (P<0.001). In the 28 day-old rats, xenon depressed c-Fos expression in response to formalin by 34% in laminae I-II (P<0.001), by 27% in lamina III-IV (P<0.001) and by 28% in lamina V-VI (P <0.001). In adult rats xenon inhibited c-Fos expression by 41% in laminae I-II (P<0.001), by 45% in lamina III-IV (P<0.001) and by 34% in lamina V-VI (P<0.001). Saline injection also caused c-Fos expression ipsilateral to the injection; however, this was much less intense than that induced by formalin injection (FIGS. 5 and 6).

Control Study

Figure 7:
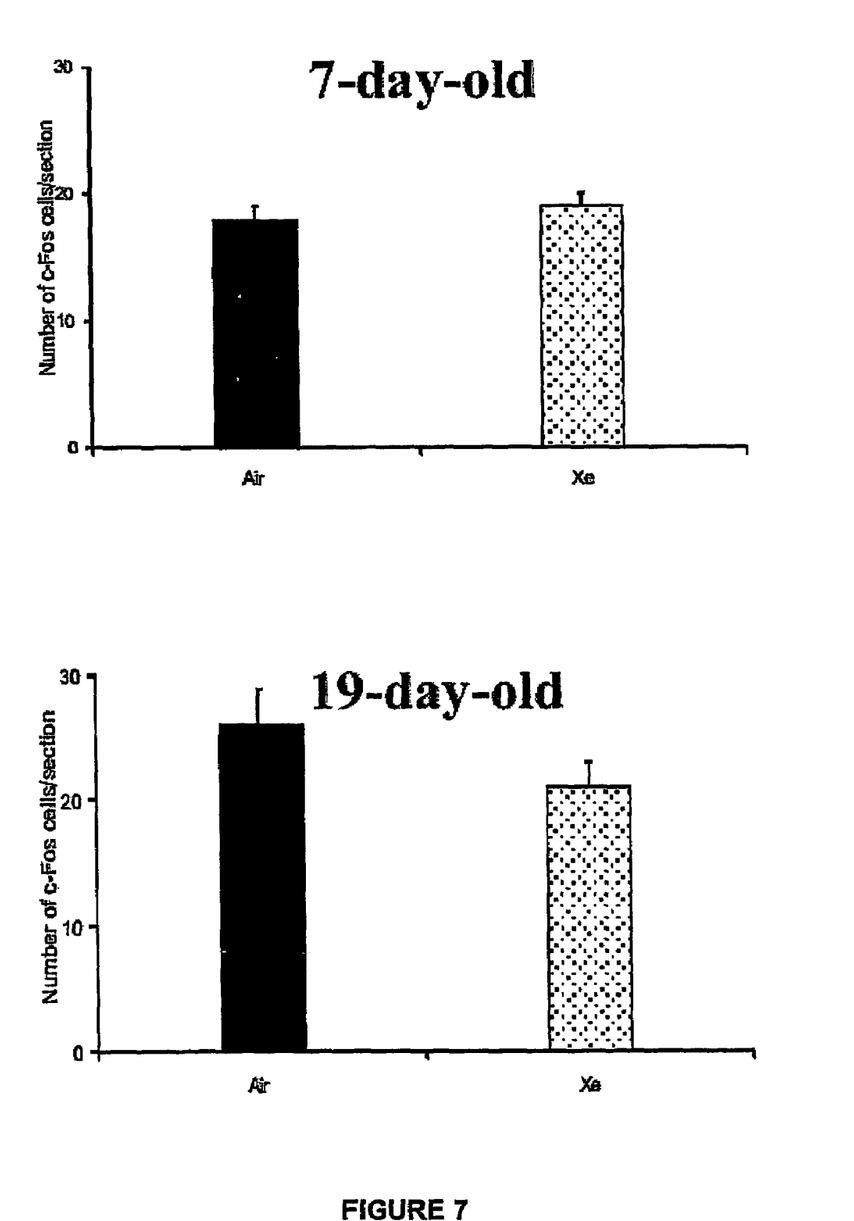
FIG. 7 shows the total number (mean±SEM, n=3) of c-Fos positive cells per section at the lumbar level of the spinal cord from the four age-groups animals receiving either air (block bar) or 70% xenon /20% $O_2$/10% $N_2$ (Xe) (dot bar). No differences were found between the corresponding age group.

In order to test whether xenon itself can cause c-Fos expression (as is the case with nitrous oxide) [Hashimoto T et al, Anesthesiology 2001;95:463-9], naïve animals were exposed to either air or the xenon mixture gas (70% Xe/20% $O_2$/10% $N_2$) for 90 min (FIG. 7). The number of c-Fos positive cells did not differ between these groups in any region of the spinal cord.

Discussion

The present study demonstrates that xenon exerts an antinociceptive response against formalin injection in Fischer rats at each of four developmental stages, i.e. at days 7, 19 and 28 day as well as in adults. These data are qualitatively different from those recently reported with $N_2O$ [Ohashi Y et al, Pain 2002;100:7-18] in which no antinociceptive effect (neither behaviorally nor immunohstochemically) was noted in animals younger than 23 days old.

In various in vitro preparations xenon and $N_2O$ are known to exert similar effects at nicotinic acetylcholine [Yamakura T et al, Anesthesiology 2000;93:1095-101], serotonin 3A [Suzuki T et al, Anesthesiology 2002;96:699-704], GABA [Yamakura T et al, Anesthesiology 2000;93:1095-101; Mennerick S et al, J. Neurosci 1998;18:9716-26], and glycine receptors [Daniels S et al, Toxicol. Lett. 1998;100-101:71-6] and both xenon [Franks N P et al, Nature 1998;396:324; de Sousa S L et al, Anesthesiology 2000;92:1055-66] and $N_2O$ [Jevtovic-Todorovic V et al, Nat Medicine 1998;4:460-63] are inhibitors of the NMDA receptor. Previous studies revealed that xenon and $N_2O$ suppressed wide dynamic range (WDR) neurons within the intact spinal cord [Utsumi J et al, Anesth Analg. 1997;84:1372-6]. However, xenon exhibited a greater inhibitory effect on these neurons in spinal cord-transected preparation than was seen after $N_2O$ exposure [Miyazagi Y et al, Anesth Analg 1999;88:893-7]. These studies suggest that xenon directly inhibits WDR neurons at the spinal level to produce antinociception while $N_2O$-induced antinociception requires involvement of higher supra-spinal centres [Fujinaga M et al, Mol Neurobiol. 2002;25:167-89]. $N_2O$ modulates nociception primarily by activation of noradrenergic descending inhibitory neurons from supra-spinal centres with little direct action, at the level of the spinal cord [Fujinaga M et al, Mol Neurobiol. 2002;25:167-89]. Given the evidence for an absolute requirement for functional connectivity between the spinal and supra-spinal regions for $N_2O$-induced antinociception, the applicants predicted and subsequently confirmed that $N_2O$ does not exhibit antinociception [Ohashi Y et al, Pain 2002;100:7-18] before development of such connectivity, i.e., below 23 days of age [Fitzgerald M et al, Brain Res 1986;389:261-70]. Thus, in contrast to xenon, $N_2O$ is not an effective antinociceptive agent in the neonatal age group.

The NMDA subtype of the glutamate receptor has been implicated in the nociceptive response to most inflammatory models of pain including that induced by formalin [Malmberg A B et al, Pain 2003;101:109-16]. As both xenon and $N_2O$ are NMDA antagonists, the reason for the qualitative differences in antinociception that exists between these two compounds is unclear. One possible explanation is that different NMDA receptor subunit combinations have different sensitivities to xenon or $N_2O$. Human endogenous NMDA receptors are composed of a combination of NR1 and NR2 or NR3 subunits [Dingledine R et al, Pharmacol Rev 1999;51:

7-61]. Of relevance, the NR2B subunit is postulated to mediate nociceptive transmission in the dorsal horn of the spinal cord [Boyce S et al, Neuropharmacology 1999;38:611-23] and forebrain [Wei F et al, Nat Neurosci 2001;4:164-9]. Of note NR2B antagonists have been linked to sedation [Chizh B A et al, Neuropharmacology 2001;40:212-20] and xenon is a more potent sedative-hypnotic agent than $N_2O$ [Lynch C et al, Anesthesiology 2000;92:865-70] with a MAC-awake of 33% [Goto T et al, Anesthesiology 2000;93:1188-93].

Based on these findings, xenon is expected to be an effective antinociceptive agent from a very early age in humans. Xenon's safety profile has yet to be examined in the very young, although it is a remarkably safe anesthetic in adults [Rossaint R et al, Anesthesiology 2003;98:6-13]. A major cause for concern in the clinical use of NMDA antagonists is their inherent neurotoxicity [Olney J W et al, Science 1989; 244:360-2; Olney J W et al, Science 1991;254:1515-8], but this does not appear to exist with administration of xenon [Ma D et al, Br J Anaesth 2002;89:739-46], a similarity shared with NR2B selective NMDA antagonists [Gill R et al, J Pharmacol Exp Ther. 2002;302:940-8].

By way of summary, formalin administration produces a typical nociceptive response observed both behaviorally and immunohistochemically ipsilateral to the site of injection in each age group tested. Xenon suppresses both the behavioural and the immunohistochemical nociceptive responses even in very young animals. Unlike $N_2O$, the antinociceptive effect of xenon does not appear to require functional connectivity between the supra-spinal and spinal pain processing pathways.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in chemistry or related fields are intended to be within the scope of the following claims.

TABLE 1

The area under curve (AUC) (mean ± SEM, n = 3-4) was calculated from nociceptive intensity scoring curves (FIG. 4).

|  | Air + formalin | 70% Xe + formalin | Air + saline |
| --- | --- | --- | --- |
| 7-day-old | 11(0.4) | 0.17(0.04)** | 0.15(0.04)** |
| 19-day-old | 88(8) | 5(0.9)* | 4.6(1.2)* |
| 28-day-old | 81(7) | 1.0(0.3)** | 5(0.5)** |
| Adult | 120(0.7) | 0.8(0.1)** | 0.4(0.1)** |

*$P < 0.01$,
**$P < 0.001$ relative to Air + formalin group at the corresponding aged-group

The invention claimed is:

1. A method of providing analgesia in a human newborn subject, the method comprising administering a therapeutically effective amount of an analgesic to a human newborn subject experiencing pain or stress sufficient to necessitate administration of the analgesic, wherein the analgesic is xenon.

2. The method of claim 1 wherein the newborn subject is a mammal in the first four weeks after birth.

3. The method of claim 1 wherein the xenon is administered in combination with a sedative, an anaesthetic agent or a further analgesic agent.

4. The method of claim 1 wherein the medicament is in gaseous form.

5. The method of claim 1 wherein the medicament is in liquid form.

6. A method accordingly to claim 1 wherein the xenon is administered in combination with a pharmaceutically acceptable carrier, diluent or excipient.

7. A method according to claim 1 wherein the xenon is administered in the form of a 20 to 70% v/v xenon/air mixture.

8. A method according to claim 1 wherein the xenon is administered in the form of a lipid emulsion.

9. A method according to claim 1 wherein the xenon is administered intraveneously, neuraxially or transversally.

10. A method of providing analgesia in a human fetal subject, the method comprising administering a therapeutically effective amount of an analgesic to a mother of a human fetal subject, the fetal subject experiencing pain or stress sufficient to necessitate administration of the analgesic, wherein the analgesic is xenon.

11. A method accordingly to claim 1 wherein the xenon is administered in combination with a pharmaceutically acceptable carrier, diluent or excipient.

12. A method according to claim 10 wherein the xenon is administered in the form of a 20 to 70% o v/v xenon/air mixture.

13. A method according to claim 10 wherein the xenon is administered in the form of a lipid emulsion.

14. A method according to claim 10 wherein the xenon is administered intraveneously, neuraxially or transdermally.

15. The method according to claim 10, wherein the xenon is administered to the mother prior to labor.

16. The method according to claim 10, wherein the xenon is administered to the mother during labor.

17. The method of claim 3, wherein the further analgesic agent is an alpha-2-adrenergic agonist, an opiate, or a non-steroidal anti-inflammatory drug.

18. The method of claim 3, wherein the sedative or anaesthetic agent promotes GABAergic activity.

* * * * *

UNITED STATES PATENT AND TRADEMARK OFFICE
CERTIFICATE OF CORRECTION

PATENT NO. : 7,632,872 B2 Page 1 of 1
APPLICATION NO. : 10/524316
DATED : December 15, 2009
INVENTOR(S) : Franks et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 164 days.

Signed and Sealed this

Second Day of November, 2010

David J. Kappos
*Director of the United States Patent and Trademark Office*